(12) United States Patent
Das

(10) Patent No.: US 6,505,081 B1
(45) Date of Patent: *Jan. 7, 2003

(54) CARDIAC PACEMAKER LEAD WITH SWAGED DISTAL ELECTRODE

(75) Inventor: Stephen D. Das, Lake Jackson, TX (US)

(73) Assignee: Intermedics, Inc., Angleton, TX (US)

( * ) Notice: Subject to any disclaimer, the term of this patent is extended or adjusted under 35 U.S.C. 154(b) by 17 days.

This patent is subject to a terminal disclaimer.

(21) Appl. No.: 09/669,824

(22) Filed: Sep. 26, 2000

Related U.S. Application Data (63) Continuation of application No. 09/036,100, filed on Mar. 6, 1998, now Pat. No. 6,148,237.

(51) Int. Cl.⁷ .................................................. A61N 1/05
(52) U.S. Cl. ..................................................... 607/122
(58) Field of Search ................................. 607/116, 119, 607/122, 123, 125–128; 600/373–377

(56) References Cited

U.S. PATENT DOCUMENTS

| | | | |
|---|---|---|---|
| 2,802,257 A | | 8/1957 | Holtzapple |
| 4,135,518 A | * | 1/1979 | Dutcher ...................... 607/122 |
| 4,328,812 A | | 5/1982 | Ufford et al. |
| 4,538,623 A | * | 9/1985 | Proctor et al. ............... 607/122 |
| 4,567,901 A | | 2/1986 | Harris |
| 4,585,013 A | | 4/1986 | Harris et al. |
| 4,944,088 A | * | 7/1990 | Doan et al. .................. 607/122 |
| 5,129,404 A | | 7/1992 | Spehr et al. |
| 5,408,744 A | * | 4/1995 | Gates .......................... 607/119 |
| 6,052,625 A | * | 4/2000 | Marshall ...................... 607/122 |
| 6,148,237 A | * | 11/2000 | Das .............................. 607/122 |
| 6,167,314 A | * | 12/2000 | Fischer, Sr. et al. ........ 607/119 |

FOREIGN PATENT DOCUMENTS

| | | | |
|---|---|---|---|
| EP | 0622090 | 11/1994 | ............ A61N/1/05 |

* cited by examiner

*Primary Examiner*—George R. Evanisko
(74) *Attorney, Agent, or Firm*—Schwegman, Lundberg, Woessner & Kluth, P.A.

(57) ABSTRACT

A cardiac stimulator lead is provided. The cardiac stimulator lead includes a connector for connecting to a cardiac stimulator and a flexible tubular sleeve that has a first end coupled to the connector and a second end. An electrode has a proximal end that is inserted into the second end of the sleeve. An annular member is disposed around the proximal end and the second end and is deformed to clamp the second end to the proximal end. A conductor wire is coupled between the connector and the electrode. The deformed annular member eliminates reliance on an adhesive-to-metal molecular bond as the sole or primary mechanism for securing the distal end of a lead sleeve to the tip electrode. Manufacturing and assembly time may be significantly reduced.

22 Claims, 4 Drawing Sheets

CARDIAC PACEMAKER LEAD WITH SWAGED DISTAL ELECTRODE

CROSS REFERENCE TO RELATED APPLICATIONS

This application is a continuation of U.S. application Ser. No. 09/036,100 filed on Mar. 6, 1998, now issued as U.S. Pat. No. 6,148,237, the specification of which is hereby incorporated by reference.

BACKGROUND OF THE INVENTION

1. Field of the Invention

This invention relates generally to cardiac stimulator leads, and more particularly to a cardiac stimulator lead having a distal electrode secured with a swaged annular member.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

A conventional cardiac stimulator lead normally consists of an elongated, flexible, tubular, electrically insulating sleeve that is connected proximally to a connector that is adapted to couple to the header of a cardiac stimulator, and distally to a tubular tip electrode. One or more ring-type electrodes may be secured to the sleeve at various positions along the length of the sleeve. The proximal end of the sleeve is connected to the connector by application of various biocompatible adhesives applied to various portions of the connector and the sleeve. The tip electrode ordinarily consists of a tubular structure that has an increased diameter portion that forms an annular shoulder against which the distal end of the lead sleeve is abutted. The exterior surface of the tubular structure is normally smooth, as is the interior surface of the distal end of the lead sleeve.

Although a combination of crimping and adhesives is commonly employed to secure the proximal end of a lead sleeve to the connector, the connection between the distal end of the lead sleeve and the tip electrode for most conventional cardiac leads is accomplished by use of an adhesive alone. A biocompatible adhesive, such as silicone based adhesive, is applied to the exterior of the tubular structure and the distal end of the lead sleeve is slipped over the tubular structure.

Many conventional lead designs incorporate a tip electrode that is composed of a non-radiopaque material. Although the motivations for selecting a non-radiopaque material for the tip electrode are several, a principle reason for selecting such materials is their ability to resist corrosion and maintain a relatively constant threshold voltage during long term exposure to the relatively hostile endocardial environment.

There are several disadvantages associated with conventional designs for cardiac leads, and particularly the structure of the interface between the lead sleeve and the tip electrode. As noted above, a biocompatible adhesive is used as the dominant mechanism for securing the distal end of a lead sleeve to a tip electrode. To ensure that an adequate bond is formed between the adhesive and the mating surfaces of the lead sleeve and the tip electrode, most adhesives must be allowed to cure for durations of up to eight hours or more. This represents a significant bottle neck in the manufacturing and assembly process since the partially assembled lead must be set aside without further handling while the adhesive is allowed to cure.

Aside from manufacturing disadvantages, adhesives used for the sleeve-to-electrode joints may experience decreases in bond strength over time. The decrease may be caused by reactions with body fluids or tissues or may stem from inconsistent mixing and/or chemical makeup at the time of assembly. As a result, there exists a small risk that the lead sleeve may disconnect from the tip electrode in circumstances where an axial force is applied to the proximal end of the lead sleeve, such as when the lead is removed from the patient.

A lack of radiopacity is a shortcoming associated with conventional electrode tips that are composed of non-radiopaque material. Proper positioning of such leads is often a difficult task since the tips of such leads are not readily visible via fluoroscopy. In such circumstances physicians often rely on the radiopaque character of the conducting coils inside the lead as an indicator of the position of the lead tip. However, for more modern leads incorporating individual small gage conductor wires, reliance upon the fluoroscopic visibility of the conductor wire may be insufficient as such fine wires normally do not show up clearly during fluoroscopy. A possible solution to the problem involves the incorporation of one or more radiographic markers into the lead sleeve. This technique involves additional expense and potentially complex manufacturing processes.

The present invention is directed to overcoming or reducing one or more of the foregoing disadvantages.

SUMMARY OF THE INVENTION

In accordance with one aspect of the present invention, a cardiac stimulator lead is provided. The cardiac stimulator lead includes a connector for connecting to a cardiac stimulator and a flexible tubular sleeve that has a first end coupled to the connector and a second end. An electrode that has a proximal end is inserted into the second end. An annular member is disposed around the proximal end and the second end and is deformed to clamp the second end to the proximal end. A conductor wire is coupled between the connector and the electrode.

In accordance with another aspect of the present invention, a cardiac stimulator lead is provided. The cardiac stimulator lead includes a connector for connecting to a cardiac stimulator and a flexible tubular sleeve that has a first end coupled to the connector and a second end. An electrode is provided that has a proximal end inserted into the second end. The proximal end has a plurality of grooves formed on the exterior thereof. An annular member is disposed around the proximal end and the second end and is deformed to clamp the second end to the proximal end such that portions of the sleeve are deformed into the grooves. A conductor wire is coupled between the connector and the electrode.

In accordance with still another aspect of the present invention, a tip electrode assembly for connecting to a flexible tubular sleeve of a cardiac stimulator lead is provided. The tip electrode assembly includes an electrode that has a proximal end for insertion into the sleeve and an annular member adapted to be positioned around the sleeve and the proximal end and deformed to clamp the sleeve to the proximal end.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
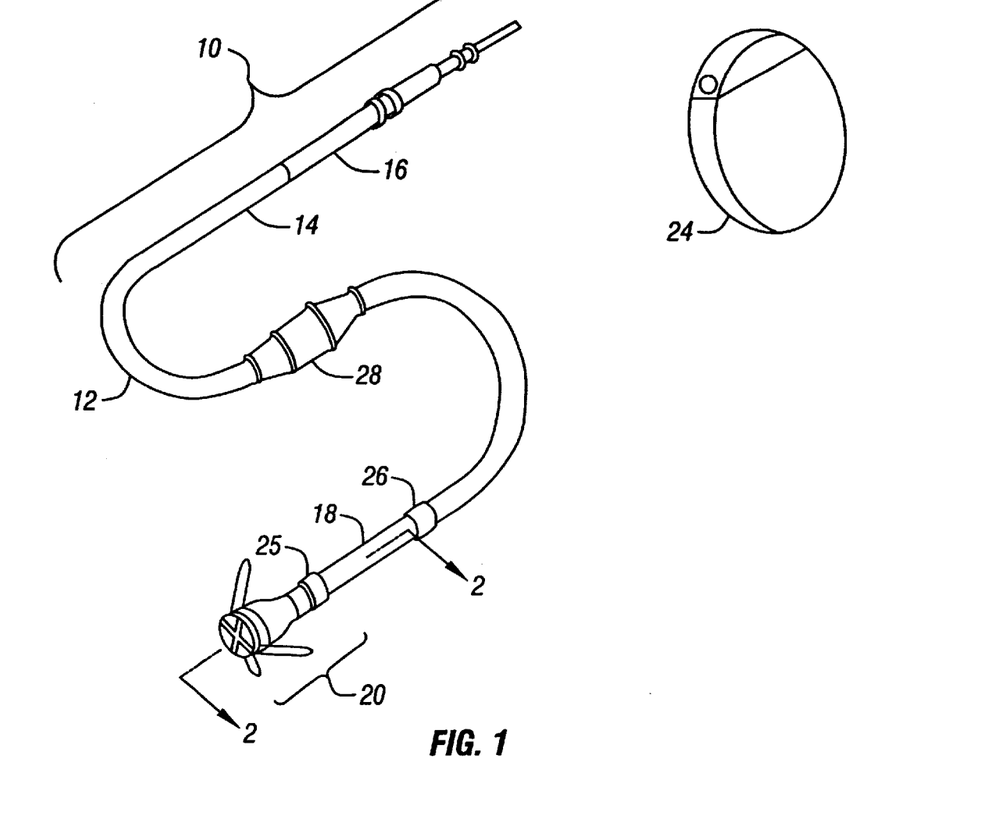
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac lead 10 that includes a flexible insulating sleeve 12 that has a proximal end 14 coupled to a connector 16, and a distal end 18 coupled to a tip electrode assembly 20. The connector 16 is designed to be inserted into a cardiac stimulator 24, and is shown highly exaggerated in size relative to the cardiac stimulator 24. The cardiac stimulator 24 may be a pacemaker, a cardioverter/defibrillator, or other type of stimulator or a sensing instrument. The tip electrode assembly 20 includes an annular member 25 to aid in securing the sleeve 12 to the electrode assembly 20 as described more fully below. The illustrated embodiment of the lead 10 is bipolar. Accordingly, the distal end 18 is provided with an electrode 26 located proximal to the tip electrode assembly 20. However, unipolar arrangements are possible as well. A suture sleeve 28 is slipped over the sleeve 12. During implantation, the suture sleeve 28 is sewn to body tissue at the site of transvenous entry.

The sleeve 12 is a flexible tubular member that provides a robust, electrically insulating coupling between the connector 16 (see FIG. 1) and the electrode assembly 20. The sleeve 12 protects one or more fine gage conductor wires enclosed therein from body fluids and tissues. The sleeve 12 is advantageously composed of a biocompatible, electrically insulating material, such as silicone, polyurethane, or like materials.

Figure 2:
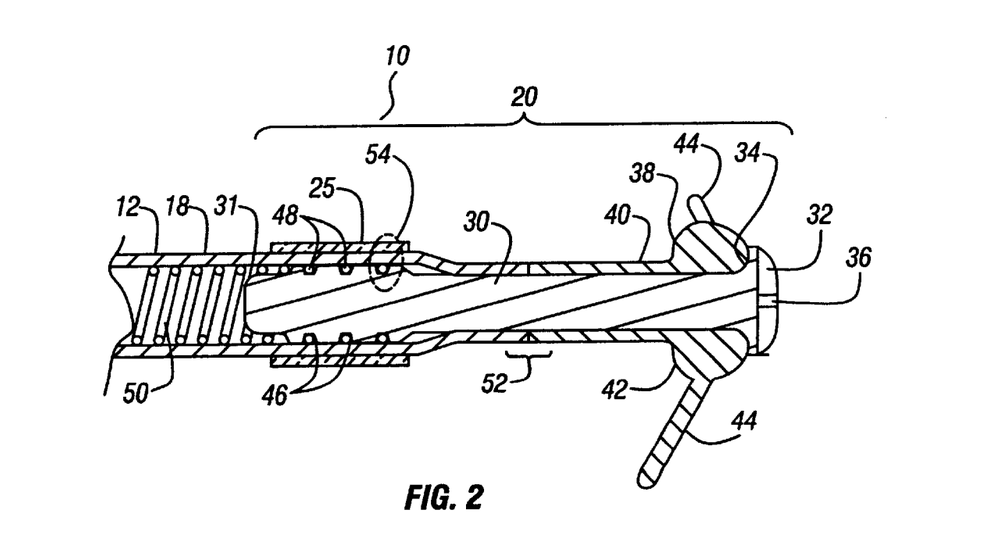
FIG. 2 is a cross-sectional view of the cardiac lead of FIG. 1 taken at section 2—2 in accordance with the present invention.

The detailed structure of the tip electrode assembly 20 may be understood by referring now to FIG. 2, which is a cross-sectional view of FIG. 1 taken at section 2—2. The electrode assembly 20 includes an elongated conducting electrode 30 secured to the sleeve 12 by the annular member 25. A distal end 32 of the electrode 30 is provided with an expanded diameter to establish an annular shoulder 34 facing proximally. The distal end 32 is designed to transmit electrical signals to and from myocardial tissue. To increase the surface area of the end 32 exposed to myocardial tissue, and thereby enhance the ability of the end 32 to transmit electrical signals, the end 32 is provided with one or more slots 36. A tine assembly 38 is disposed over the electrode 30. The tine assembly 38 includes a supporting body 40 composed of a suitable biocompatible insulating material, such as silicone, polyurethane, or like materials. The body 40 may be injection molded around the electrode 30 or separately molded and slipped over the electrode 30. The body 40 includes a bulbous portion 42 which abuts the annular shoulder 34. Two or more tines 44 project radially outwardly from the bulbous portion 42 and may be integrally molded with the body 40 or separately molded and coupled thereto.

The proximal end 31 of the electrode 30 is inserted into the distal end 18 of the sleeve 12 so that the proximal end of the supporting body 40 abuts the distal end 18 at 52. The proximal end 31 is provided with a set of external grooves 46 that are configured much like the external threads of a typical bolt or machine screw. The grooves 46 provide spaces to receive protruding portions of the distal end 18 of the sleeve 12 as described below.

The distal coils 48 of a conductor wire 50 may be spiraled around the proximal end 31, disposed in the grooves 46 and secured to the electrode 30 by laser welding, other like welding techniques, or other suitable fastening methods. The proximal end 31 of the electrode 30 is provided with a slightly larger diameter than the inner diameter of the coils 48 of the wire 50. The distal coils 48 may be connected to the electrode 30 by first urging the coils 48 over the slightly larger diameter proximal end 31 and then threading the coils 48 into the channels 46 by rotating the wire 50 and/or the electrode 30. Alternatively, the distal coils 48 may be coupled to the proximal end 31 without engaging the channels 46. In either circumstance, the location and number of the welds is a matter of design discretion. The conductor wire 50 is connected proximally to the connector 16 shown in FIG. 1 by welding or other suitable technique.

The conductor wire 50 is depicted as a single individually insulated wire with insulation removed from the coils 48 so that electrical contact is established between the wire 50 and the tip electrode 30. However, the skilled artisan will appreciate that the conductor wire 50 may not be individually insulated if the lead 10 is unipolar or if the various conductor wires in the lead 10 are coaxially arranged or arranged in a nested configuration. Another conductor wire (not shown) couples the electrode 26 shown in FIG. 1 to the connector 16.

Figure 3:
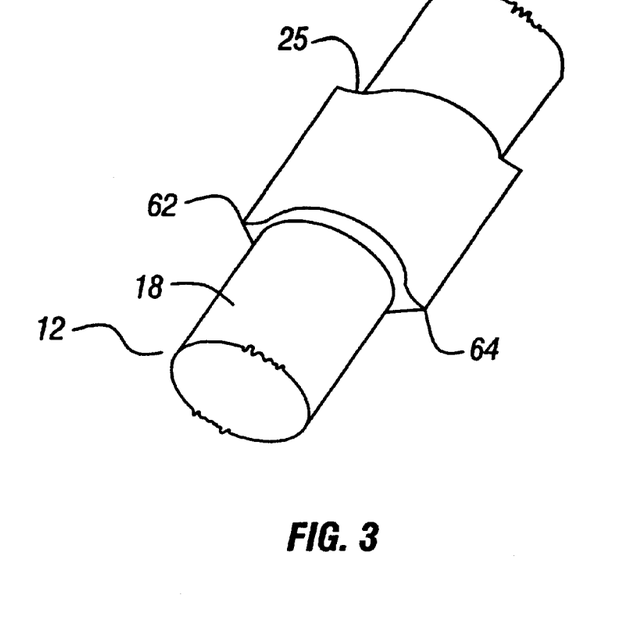
FIG. 3 is a close-in pictorial view of a portion of the lead shown in FIG. 1 depicting the annular member in accordance with the present invention.
Figure 4:
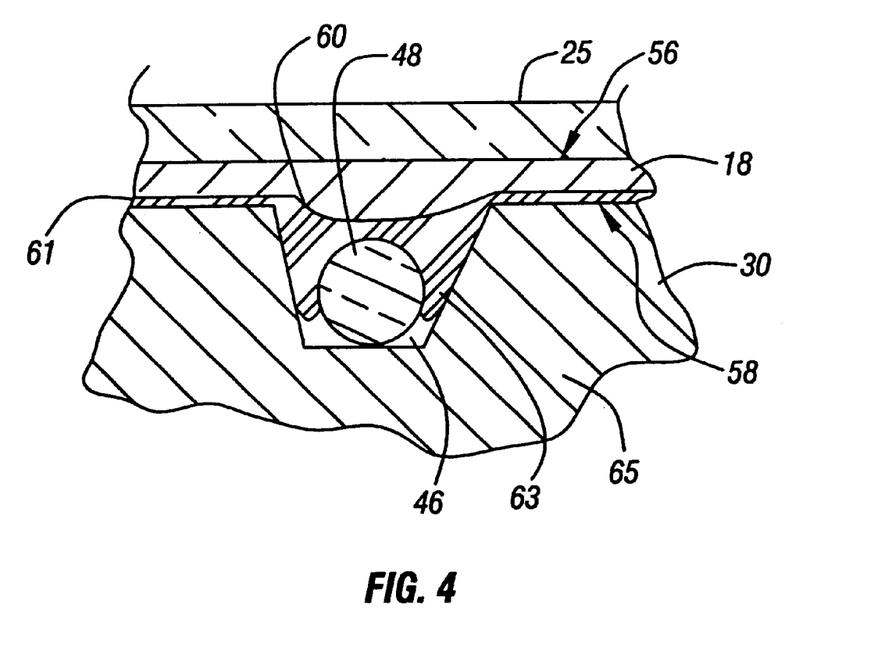
FIG. 4 is a detailed cross-sectional view of a designated portion of the lead shown in FIG. 2 in accordance with the present invention.

The detailed interaction between the annular member 25, the distal end 18, and the electrode 30 may be understood by referring now also to FIGS. 3 and 4. FIG. 3 is a close up pictorial view of the distal end 18 and the annular member 25, and FIG. 4 is a detailed view of the portion of the lead 10 circumscribed by the dashed oval 54 in FIG. 2. The annular member 25 is slipped over the sleeve 12 and positioned around the channels 46. The annular member 25 is then deformed to snugly secure the distal end 18 to the electrode 30. The deformation decreases the internal diameter of the annular member 25. The distal end 18 is pinched between the internal surface 56 of the annular member 25 and the external surface 58 of the electrode 30. As a result of the pinching action and the elastomeric character of the distal end 18, a portion of the distal end 18 designated generally at 60 will protrude into each channel 46. Depending upon whether a distal coil 48 is disposed in the groove 46, and upon the diameter of the distal coil 48, the protruding portion 60 may or may not bear against the distal coil 48. Preferably, a medical adhesive 61 has been placed between the distal end 18 and the electrode 30. The adhesive may be a suitable medical grade adhesive, such as silicone based adhesive, a two-part adhesive, or similar adhesives. When the adhesive has cured, the pinching of the annular member 25 forces the adhesive into the groove 46. The adhesive forms a secure molecular bone with the distan end 18 and a secure mechanical bond with the electrode 30 by forming ridges 63. The presence of the annular member 25 thereafter prevents the distal end from expanding and keeps the riges 63 in the groove 46. Use of the adhesive is important where the sleeve is formed of low durometer material, such as silicon. It can be omitted where the sleeve if formed of stiffer material, such as polyurethane.

The objective of the deformation operation is to reduce the internal diameter of the annular member 25 sufficiently to pinch and secure the distal end 18 to the electrode 30. The manner in which the annular member 25 is deformed to produce the desired internal diameter may be varied and is a matter of design discretion. In the embodiment depicted in FIGS. 3 and 4, the deformation of the annular member 25 is advantageously provided by crimping. The crimping produces radially projecting ridges 62 and 64 of material formed on opposite sides of the annular member 25.

The annular member 25 provides both frictional and mechanical retention of the distal end 18 to the electrode 30. The clamping action provides a snug interference fit between the interior surface 56 of the distal end 18 and the exterior surface 58 of the electrode 30. In addition, the various protrusions 60 of the distal end 18 forcibly engage the walls 65 of their respective channels 46 to provide a secure mechanical engagement between the distal end 18 and the electrode 30.

The cured medical adhesive 61 completes the assembly be a very secure mechanical engagement with the electrode 30 and a very secure molecular engagement with the distal end 18. It is, therefore, not necessary to rely on the inherently weaker molecular bond between the adhesive and the metal electrode 30.

Figure 5:
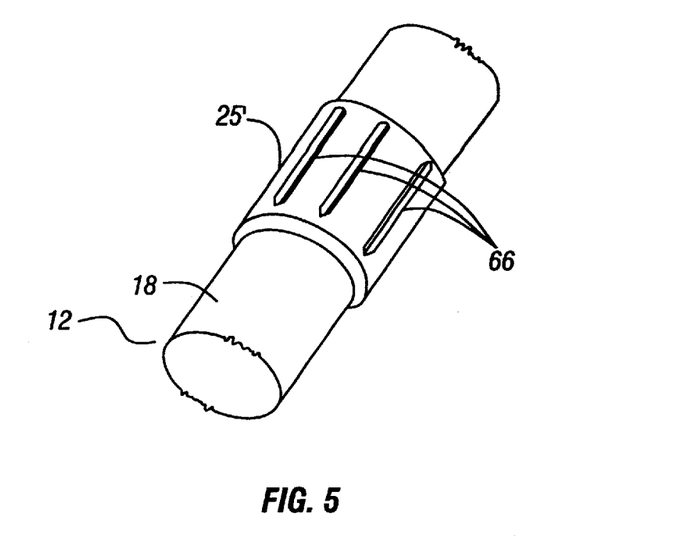
FIG. 5 is a view like FIG. 3 of an alternate embodiment of an annular member in accordance with the present invention.
Figure 6:
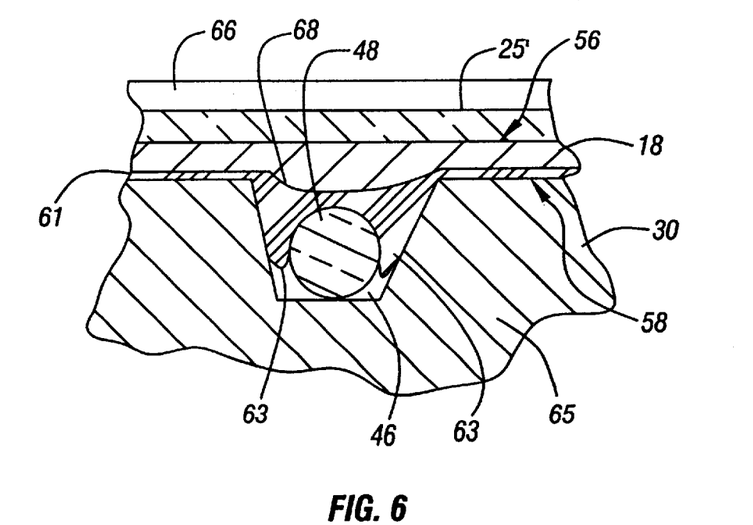
FIG. 6 is a view like FIG. 4 depicting the alternate annular member in accordance with the present invention.

In an alternate embodiment illustrated in FIGS. 5 and 6, the deformation of the annular member, now designated 25', is produced in a different crimping operation. FIG. 5 is a view like FIG. 3 and FIG. 6 is a view like FIG. 4. In this embodiment, the annular member 25' is crimped to yield several circumferentially spaced grooves 66 in the exterior surface of the annular member 25' and an attendant decrease in the internal diameter of the annular member 25' in the vicinity of the grooves 66. The number, size and spacing of the grooves 66 is largely a matter of design discretion. In those areas where the internal diameter of the annular member 25' is decreased, the distal end 18 will be pinched between the internal surface 56 of the annular member 25' and the external surface 58 of the electrode 30. As a result of the pinching action and the elastomeric character of the distal end 18, a portion of the distal end 18 designated generally at 68 will protrude into each channel 46. Each protrusion 68 will generally be positioned directly beneath the groove 66 and extend to some distance on either side of the groove 66. Depending upon the diameter of the distal coil 48, the protruding portion 68 may or may not bear against the distal coil 48. The adhesive 61 will also be forced into the groove forming the ridges 63, as described above.

Like the annular member described above, the annular member 25' provides both frictional and mechanical retention of the distal end 18 to the electrode 30. The clamping action provides a snug interference fit between the interior surface 56 of the distal end 18 and the exterior surface 58 of the electrode 30. In addition, the various protrusions 68 of the distal end 18 forcibly engage the walls 65 of their respective channels 46 to provide a secure mechanical engagement between the distal end 18 and the electrode 30.

The skilled artisan will appreciate that deformation techniques other than crimping may be used to clamp the annular members 25 and/or 25' to the distal end 18. For example, the desired deformation may be accomplished by swaging. When swaged, the annular members 25 and/or 25' will increase in length slightly as a result of deformation into a smaller internal diameter.

The electrode 30 may be fabricated from a variety of biocompatible conducting materials, such as iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material. The annular member 25 may be fabricated from the same types of materials. However, while sufficient ductility to enable ready deformation is desirable, high electrical conductivity is not required. The annular member 25 may be fabricated from a radiopaque material where the electrode 30 is not fabricated from a radiopaque material or where it is desired to provide the lead 10 with enhanced radiopaque characteristics.

Figure 7:
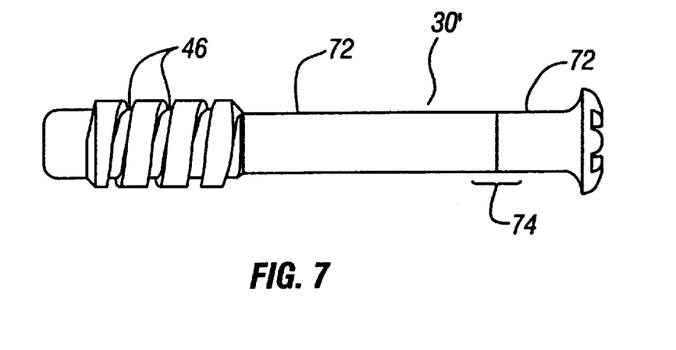
FIG. 7 is a side view of an alternate tip electrode embodying a two-part electrode in accordance with the present invention.

FIG. 7 depicts a side view of an alternate embodiment of the electrode, now designated 30'. The electrode 30' includes a tip member 70 coupled to a tubular shank 72 at 74. The connection at 74 may be by welding, threaded connection, or other suitable connection method. The tip member 70 is composed of a non-radiopaque material, such as, for example, iridium oxide coated titanium or other suitable conducting non-radiopaque material. The shank 72 may be composed of a radiopaque material, such as, for example, platinum iridium alloy (90% platinum, 10% iridium) or other suitable conducting radiopaque material. This embodiment provides a radiopaque electrode to facilitate fluoroscopic observation where the annular member 25 described above is not composed of a radiopaque material or where additional radiopaque characteristics are desired.

Figure 8:
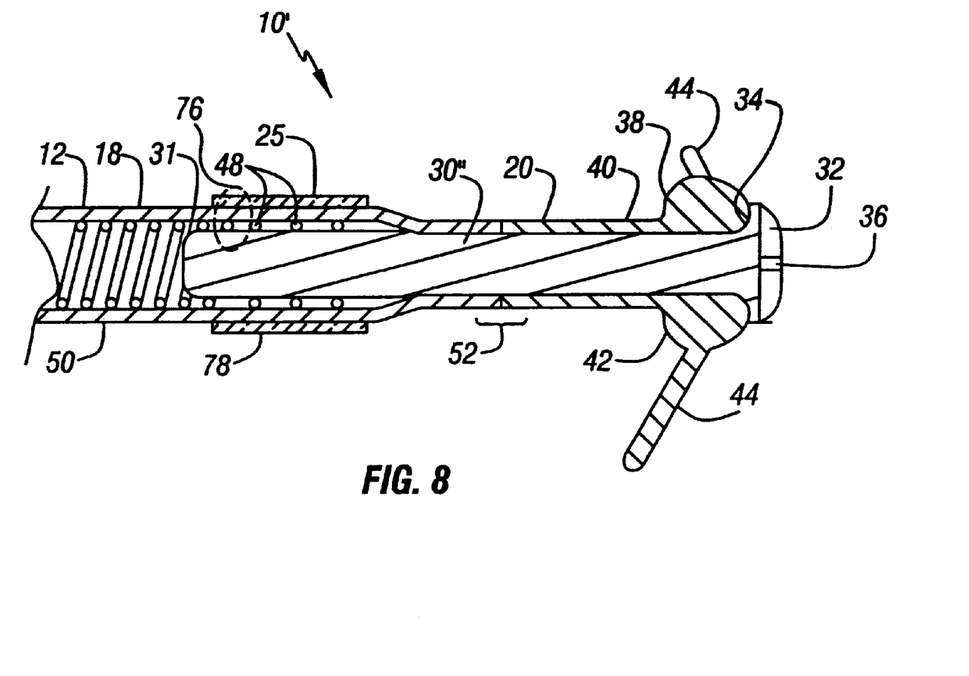
FIG. 8 is a cross-sectional view like FIG. 2 depicting an alternate embodiment of the cardiac stimulator lead of FIG. 1 in accordance with the present invention.
Figure 9:
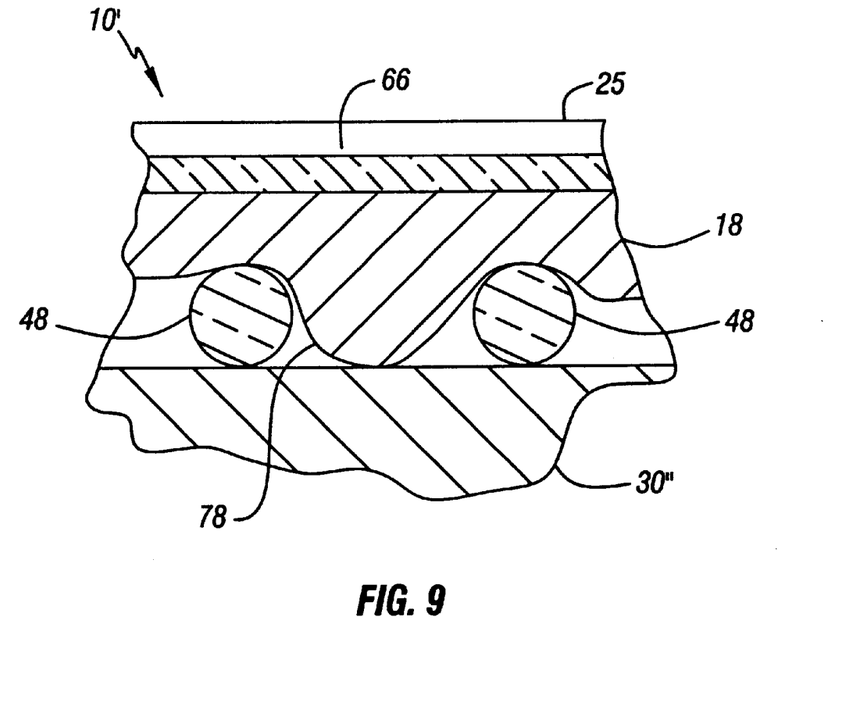
FIG. 9 is a detailed cross-sectional view of a designated portion of the lead shown in FIG. 8 in accordance with the present invention.

FIG. 8 depicts a cross-sectional view like FIG. 2 of an alternate embodiment of the lead, now designated 10', and FIG. 9 depicts a detailed view of the portion of the lead 10', circumscribed by the dashed oval 76. In this embodiment, the electrode, now designated 30", is configured with a generally smooth, isodiametric exterior surface and is not provided with the aforementioned channels or threads. The annular member 25 is positioned and deformed as described above. The deformation yields protrusions 78 in the distal end 18 of the sleeve 12 (one of which is shown in FIG. 9) that are disposed between individual coils 48 and bear against the exterior surface of the proximal end 31, providing a friction engagement between the proximal end 31 and the protrusions 78. As with the aforementioned embodiment, a suitable medical grade adhesive may be applied between the distal end 18 and the electrode 30" to provide a seal against the intrusion of body fluids and to provide a complimentary mechanism to secure the distal end 18 to the electrode 30".

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac stimulator lead, comprising:
   a connector adapted to connect to a cardiac stimulator;
   a flexible tubular sleeve having a first end and a second end, and the first end is coupled to the connector;
   an electrode having a proximal end inserted into the second end;
   an annular member disposed around the proximal end of the electrode and the second end of the flexible tubular sleeve deformed over the sleeve to clamp the second end of the sleeve to the proximal end;
   a conductor wire coupled between the connector and the electrode; and
   the electrode having at least one spiral groove, and portions of the sleeve are compressed into at least one groove by the deformed annular member disposed around at least a portion of the spiral groove.

2. The cardiac stimulator of claim 1, wherein the proximal end of the electrode has a first outer diameter, the conductor is a coil having a second inner diameter, and the first diameter is greater than the second diameter.

3. The cardiac stimulator lead as recited in claim 1, wherein the annular member comprises a crimped annular member deformed over the sleeve.

4. The cardiac stimulator lead as recited in claim 1, wherein the annular member comprises a swaged annular member deformed over the sleeve.

5. The cardiac stimulator lead as recited in claim 1, wherein the annular member is mechanically and molecularly engaged with the electrode.

6. The cardiac stimulator lead as recited in claim 1, wherein the electrode further includes a plurality of spiral grooves and a distal end of the sleeve is deformed into the plurality of grooves of the electrode.

7. The cardiac stimulator lead as recited in claim 1, wherein the lead includes, and adhesive forced into the groove by the annular member.

8. The cardiac stimulator lead as recited in claim 7, wherein the adhesive forms a molecular bond with the sleeve and a mechanical bond with the electrode.

9. The cardiac stimulator lead as recited in claim 1, wherein the sleeve includes protrusions forcibly engaging walls of the at least one groove.

10. A cardiac stimulator lead, comprising:
    a connector adapted to connect to a cardiac stimulator;
    a flexible tubular sleeve having a first end and a second end, and the first end is coupled to the connector;
    an electrode having a proximal end inserted into the second end;
    an annular member disposed around the proximal end of the electrode and the second end of the flexible tubular sleeve and deformed over the sleeve to clamp the second end of the sleeve the proximal end;
    a conductor wire coupled between the connector and the electrode; and
    a medical adhesive disposed adjacent to the wire and forming a ridge adjacent to the wire wherein the proxial end of the electrode has a plurality of grooves and portions of the sleeve are compressed into the grooves by the annular member.

11. A cardiac stimulator lead, comprising:
    a connector adapted to connect to a cardiac stimulator;
    a flexible tubular sleeve having a first end and a second end, and the first end is coupled to the connector;
    an electrode having a proximal end inserted into the second end;
    an annular member disposed around the proximal end of the electrode and the second end of the flexible tubular sleeve and deformed over the sleeve to clamp the second end of the sleeve to the proximal end;
    a conductor wire coupled between the connector and the electrode; and
    the annular member has a plurality of grooves formed therein.

12. The cardiac stimulator lead as recited in claim 11, wherein the grooves comprise circumferentially spaced grooves in the exterior surface of the annular member.

13. A cardiac stimulator lead comprising:
    a connector adapted to connect with a cardiac stimulator;
    a flexible tubular sleeve having a first end and a second end, the first end is coupled to the connector;
    an electrode having a proximal end inserted into the second end, the proximal end of the electrode has a plurality of electrode grooves;
    an annular member disposed and deformed around the proximal end of the electrode and the second end of the flexible tubular sleeve, portions of the sleeve are compressed into the electrode grooves by the annular member, the annular member having a plurality of grooves formed therein; and
    a conductor wire coupled between the connector and the electrode.

14. The cardiac stimulator lead of claim 13, further comprising means for bonding the flexible tubular sleeve with the electrode.

15. The cardiac stimulator lead of claim 13, wherein the proximal end of the electrode has a first outer diameter, the conductor is a coil having a second inner diameter, and the first diameter is greater than the second diameter.

16. The cardiac stimulator lead of claim 13, wherein the electrode comprises a tip member coupled to a tubular shank, the tubular shank being composed of a radiopaque material.

17. The cardiac stimulator lead as recited in claim 13, wherein the distal end of the sleeve is permanently deformed into grooves of the electrode.

18. The cardiac stimulator lead as recited in claim 13, wherein the second end of the sleeve protrudes into said electrode grooves.

19. A cardiac stimulator lead comprising:

a connector adapted to connect with a cardiac stimulator;

a flexible tubular sleeve having a first end and a second end, the first end is coupled to the connector;

an electrode having a proximal end inserted into the second end;

an annular member disposed around the proximal end of the electrode and the second end of the flexible tubular sleeve;

a conductor wire coupled between the connector and the electrode;

means for decreasing an inner diameter of the annular member over the flexible tubular member; and the annular member is composed of a radiopaque material.

20. The cardiac stimulator lead of claim 10, wherein the proximal end of the electrode has a plurality of grooves and portions of the sleeve are compressed into the grooves by the annular member.

21. The cardiac stimulator lead as recited in claim 13, wherein the annular member has a plurality of grooves formed therein.

22. The cardiac stimulator lead of claim 19, wherein the electrode has at least one circumferential groove, and portions of the sleeve being compressed into at least one groove by the annular member.

* * * * *

UNITED STATES PATENT AND TRADEMARK OFFICE
CERTIFICATE OF CORRECTION

PATENT NO.  : 6,505,081 B1
DATED       : January 7, 2003
INVENTOR(S) : Das

It is certified that error appears in the above-identified patent and that said Letters Patent is hereby corrected as shown below:

Column 7,
Line 60, delete "includes, and" and insert -- includes --, therefor.

Column 8,
Line 10, delete "sleeve the" and insert -- sleeve to the --, therefor.
Line 14, delete "proxial" and insert -- proximal --, therefor.

Column 10,
Line 3, delete "claim 10" and insert -- claim 19 --, therefor.
Line 7, delete "claim 13" and insert -- claim 19 --, therefor.

Signed and Sealed this

Twenty-fourth Day of June, 2003

JAMES E. ROGAN
*Director of the United States Patent and Trademark Office*